United States Patent
Hilgers et al.

(10) Patent No.: US 9,878,082 B2
(45) Date of Patent: Jan. 30, 2018

(54) METHOD AND APPARATUS FOR OPTIMIZING AN EXTRACORPOREAL BLOOD TREATMENT

(75) Inventors: Peter Hilgers, Schonungen (DE); Joerg Telcher, Bad Homburg (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 77 days.

(21) Appl. No.: 13/320,297

(22) PCT Filed: May 12, 2010

(86) PCT No.: PCT/EP2010/002945
§ 371 (c)(1),
(2), (4) Date: Dec. 9, 2011

(87) PCT Pub. No.: WO2010/130449
PCT Pub. Date: Nov. 18, 2010

(65) Prior Publication Data
US 2012/0078658 A1    Mar. 29, 2012

(30) Foreign Application Priority Data
May 14, 2009 (DE) .................. 10 2009 021 255

(51) Int. Cl.
  *G06Q 50/22* (2012.01)
  *A61M 1/16* (2006.01)
(52) U.S. Cl.
  CPC ............ *A61M 1/16* (2013.01); *A61M 1/1613* (2014.02); *G06Q 50/22* (2013.01); *A61M 2205/50* (2013.01)
(58) Field of Classification Search
  USPC ........... 705/2-4; 210/321.6-321.9, 646, 782; 604/4.01, 6.01
  See application file for complete search history.

(56) References Cited

U.S. PATENT DOCUMENTS 5,308,315 A * 5/1994 Khuri et al. ............... 604/4.01
5,319,542 A    6/1994 King et al.
(Continued)

FOREIGN PATENT DOCUMENTS

EP    1159977 A2    12/2001
EP    1614438 A2    1/2006
(Continued)

OTHER PUBLICATIONS

Locatelli et al., "Effect of Membrane Permeability on Survival of Hemodialysis Patients", JASN vol. 20 #3 (published online Dec. 17, 2008), hereinafter MPO Study.*

*Primary Examiner* — Mark Holcomb
(74) *Attorney, Agent, or Firm* — Kilyk & Bowersox, P.L.L.C.

(57) ABSTRACT

The invention relates to a method and apparatus for optimizing an extracorporeal blood treatment using an extracorporeal blood treatment apparatus, an extracorporeal blood treatment apparatus with a device for optimizing the extracorporeal blood treatment, and a computer program to be executed on a processor for carrying out a method for optimizing the extracorporeal blood treatment. The method and apparatus are characterized in that at least one machine-specific treatment parameter for carrying out the treatment using the respective dialyzer or filter is determined with a computing unit for different types of dialyzers or filters. The computing unit determines the costs resulting from the determined machine-specific treatment parameters when using the respective dialyzer or filter. The determined costs for different types of dialyzers or filters are then displayed on a display unit. The doctor can then select the dialyzer or filter to keep the costs as low as possible.

13 Claims, 11 Drawing Sheets

(56) References Cited

U.S. PATENT DOCUMENTS

| | | | |
|---|---|---|---|
| 5,609,770 | A | 3/1997 | Zimmerman et al. |
| 5,708,798 | A | 1/1998 | Lynch et al. |
| 6,117,100 | A * | 9/2000 | Powers et al. ............... 604/6.11 |
| 6,187,199 | B1 * | 2/2001 | Goldau ........................ 210/646 |
| 7,801,746 | B2 * | 9/2010 | Moll et al. ........................ 705/3 |
| 8,123,715 | B2 * | 2/2012 | Hamada et al. ................ 604/29 |
| 8,512,271 | B2 * | 8/2013 | Moissl et al. ................ 604/6.11 |
| 2003/0083901 | A1 * | 5/2003 | Bosch et al. ........................ 705/2 |
| 2010/0010423 | A1 * | 1/2010 | Yu et al. ........................ 604/29 |
| 2010/0010424 | A1 * | 1/2010 | Yu et al. ........................ 604/29 |
| 2010/0168925 | A1 | 7/2010 | Hilgers et al. |

FOREIGN PATENT DOCUMENTS

| | | |
|---|---|---|
| JP | 9-218887 A | 8/1997 |
| JP | 2000-245827 | 9/2000 |
| WO | 2007/140993 | 12/2007 |

* cited by examiner

| Costs | | | | | | | |
|---|---|---|---|---|---|---|---|
| ⊙ QB 1 | ○ QB 2 | | | FX 50 | FX 60 | FX 80 | FX 100 |
| QD | | | | 1000 | 900 | 600 | 500 |
| Kt/V | | | | 1,36 | 1,41 | 1,41 | 1,44 |
| Total Costs | | | | 21,2 | 20,57 | 17,89 | 17,26 |
| Filter prices | | | | 10,4 | 10,8 | 11,2 | 11,6 |
| Other costs | | | | 10,8 | 9,77 | 6,69 | 5,66 |
| Details of other costs | | | | | | | |
| Permeate | | | | 1,69 | 1,54 | 1,07 | 0,92 |
| Acid | | | | 2,92 | 2,64 | 1,79 | 1,51 |
| Bicarbonate | | | | 5,3 | 4,79 | 3,25 | 2,74 |
| Electricity | | | | 0,89 | 0,81 | 0,57 | 0,49 |

| Costs | | | | | |
|---|---|---|---|---|---|
| ○ QB 1 | ⊙ QB 2 | | | | |
| QD | | | 600 | 500 | 400 |
| Kt/V | | | 1,42 | 1,45 | 1,47 |
| Total Costs | | | 17,49 | 16,86 | 16,23 |
| Filter prices | | | 10,8 | 11,2 | 11,6 |
| Other costs | | | 6,69 | 5,66 | 4,63 |
| | | | FX 60 | FX 80 | FX 100 |

Details of other costs

| | | | | | |
|---|---|---|---|---|---|
| Permeate | | | 1,07 | 0,92 | 0,77 |
| Acid | | | 1,79 | 1,51 | 1,23 |
| Bicarbonate | | | 3,25 | 2,74 | 2,23 |
| Electricity | | | 0,57 | 0,49 | 0,41 |

Fig. 5

Kt/V Routenplaner V6.3 K

Therapeutic Aim — 25A
- Kt/V: 1,4
- T: 240 [min]

Patient — 25B
- Qb: 290 [ml/min]
- V: 35 [l]

Therapy Details — 25C
- Machine: 4008 / 5008
- Flows: Flows
- Filter: Manual
- Method: HD / HDF post / HDF pre
- Laboratory Data: HKT, TP, Recirculation
- FX high flux / FX low flux

Result — 25D

| Qb | Filter | Qd | Qs | sp Kt/V | b 2 m clear. | UFV [ml] |
|---|---|---|---|---|---|---|
| 290 | FX 100 | 300 | A Sub | 1,41 | 88 | 2500 |
| 320 | FX 80 | 300 | A Sub | 1,42 | 86 | 2500 | store / view / costs 24D
25

Fig. 6

Costs

○ QB 1   ○ QB 2

| | | FX 60 | FX 80 | FX 100 |
|---|---|---|---|---|
| QD | | 600 | 400 | 300 |
| Kt/V | | 1,43 | 1,41 | 1,41 |
| Total Costs | | 18,11 | 16,45 | 15,82 |
| Filter prices | | 10,8 | 11,2 | 11,6 |
| Other costs | | 7,31 | 5,25 | 4,22 |

Details of other costs

| | | | | |
|---|---|---|---|---|
| Permeate | | 1,17 | 0,86 | 0,71 |
| Acid | | 1,96 | 1,4 | 1,11 |
| Bicarbonate | | 3,56 | 2,53 | 2,02 |
| Electricity | | 0,62 | 0,46 | 0,38 |

| Costs | | | | |
|---|---|---|---|---|
| ○ QB 1 | ● QB 2 | | | |
| | | FX 60 | FX 80 | FX 100 |
| QD | | 400 | 300 | 300 |
| Kt/V | | 1,43 | 1,42 | 1,51 |
| Total Costs | | 16,15 | 15,53 | 15,93 |
| Filter prices | | 10,8 | 11,2 | 11,6 |
| Other costs | | 5,35 | 4,33 | 4,33 |
| Details of other costs | | | | |
| Permeate | | 0,88 | 0,72 | 0,72 |
| Acid | | 1,43 | 1,14 | 1,14 |
| Bicarbonate | | 2,58 | 2,07 | 2,07 |
| Electricity | | 0,47 | 0,39 | 0,39 |

METHOD AND APPARATUS FOR OPTIMIZING AN EXTRACORPOREAL BLOOD TREATMENT

CROSS REFERENCE TO RELATED APPLICATIONS

This is a 371 national phase application of PCT/EP2010/002945 filed May 12, 2010, claiming priority to German Patent Application No. 10 2009 021 255.8 filed May 14, 2009.

FIELD OF INVENTION

The invention relates to a method and a device for optimizing an extracorporeal blood treatment with an extracorporeal blood treatment apparatus, which comprises a dialyzer or filter divided by a semipermeable membrane into a first chamber and a second chamber, wherein the first chamber is part of an extracorporeal blood circuit and the second chamber of the dialyzer or filter is part of a dialyzing fluid system. Moreover, the invention relates to an extracorporeal blood treatment apparatus with a device for optimizing the extracorporeal blood treatment. The invention also relates to a computer program product to be run on a data processing device for performing a method for optimizing the extracorporeal blood treatment.

BACKGROUND OF THE INVENTION

Various methods for extracorporeal blood treatment or cleaning are used in chronic kidney failure in order to remove substances usually eliminated with urine and for fluid withdrawal. In hemodialysis, the patient's blood is cleaned outside the body in a dialyzer. The dialyser comprises a blood chamber and a dialyzing fluid chamber, which are separated by a semipermeable membrane. During the treatment, the patient's blood flows through the blood chamber, whilst dialyzing fluid flows through the dialyzing fluid chamber in order to free the patient's blood from substances usually eliminated with urine.

Whereas the transport of the low-molecular substances through the membrane of the dialyzer is essentially determined by the concentration differences (diffusion) between the dialyzing fluid and the blood in the case of hemodialysis (HD), substances dissolved in the plasma water, in particular higher-molecular substances, are effectively removed by a high fluid flow (convection) through the membrane of the dialyzer in the case of hemofiltration (HF). In hemofiltration, the dialyzer functions as a filter. Hemodiafiltration (HDF) is a combination of the two processes.

Various dialyzers or filters are known for performing extracorporeal blood treatments. The known dialyzers or filters include the so-called high-flux and low-flux dialyzers or filters. High-flux dialyzers are characterized by a higher ultrafiltration coefficient than low-flux dialyzers.

For an extracorporeal blood treatment, the doctor in charge must preselect a number of treatment parameters which on the one hand relate to the patient and on the other hand to the blood treatment apparatus used to perform the blood treatment. The treatment parameters to be preselected by the doctor are therefore referred to below as patient-specific or machine-specific treatment parameters.

In the following, patient-specific treatment parameters are understood to mean the parameters which are characteristic of the therapeutic aim and/or the patient to be treated. The doctor in charge first selects the respective therapeutic method for the patient, a distinction having to be made for example between hemodialysis (HD), hemofiltration (HF) and hemodiafiltration (HDF). Furthermore, the doctor establishes treatment time t, taking account of the individual patient's circulatory stability. Furthermore, the doctor establishes dialysis dose kt/V as the target value for the treatment. A value for dialysis dose kt/V of 1.4 generally applies as the target value for a suitable treatment. The literature also discusses higher target values for women or particularly light patients. A further patient-specific treatment parameter is the flow of blood in the extracorporeal circuit. The blood flow can be varied by the doctor within certain limits during the treatment, but ultimately the adjustable blood flow is dependent on the nature and the properties of the patient's vascular access.

In the following, the machine-specific treatment parameters are understood to mean the parameters which the doctor himself can freely select for the performance of the extracorporeal treatment, taking account of the patient-specific treatment parameters. The machine-specific treatment parameters include in particular the dialyzing fluid flow rate, which can be set freely within certain limits with the known extracorporeal blood treatment apparatuses.

Since the doctor in charge has various types of dialyzer or filter available to him for the performance of the extracorporeal blood treatment, which include for example the aforementioned high-flux and low-flux dialyzers, the doctor must select a specific dialyzer or filter before the treatment. The selection of a particular type of dialyzer, however, in turn affects the machine-specific treatment parameters which the doctor must set in order to achieve the therapeutic aim. With an unchanged blood flow, the same clearance can be achieved with a dialyzer characterized by a greater effective surface with a smaller dialyzing fluid flow rate as with a dialyzer characterized by a smaller effective surface.

The doctor in charge will select the patient- and machine-specific treatment parameters in such a way that the blood treatment can be carried out in the optimum manner for the given patient. When the doctor in charge has different types of dialyzer or filter available to him, however, there may be different parameters with which the blood treatment can be carried out in the optimum manner.

SUMMARY OF THE INVENTION

The problem underlying the invention is to provide a method for optimizing an extracorporeal blood treatment with an extracorporeal blood treatment apparatus, which makes it easier for the doctor in charge to select the respective dialyzer or filter from a group of dialyzers or filters. Moreover, it is an object of the invention to provide a device for optimizing an extracorporeal blood treatment, which makes it easier for the doctor to select the dialyzer or filter. A further object of the invention is to make available an extracorporeal blood treatment apparatus with a device for optimizing the extracorporeal blood treatment and a computer program product to be run on a data processing device for performing the method for optimizing the extracorporeal blood treatment.

The method according to the invention and the device according to the invention for optimizing an extracorporeal blood treatment are based on the fact that at least one machine-specific treatment parameter for performing the treatment using the given dialyzer or filter is determined with a computing unit for different types of dialyzer or filter, and the costs resulting from the ascertained machine-specific treatment parameter using the given dialyzer or filter are determined with the computing unit, and the ascertained costs for all the types of dialyzer or filter are displayed on a display unit. The information required for the selection to be made for the dialyzer or filter is thus made available to the doctor in charge. The doctor can then select the dialyzer or filter in such a way that the cost of the blood treatment is as low as possible.

The device according to the invention for optimizing the extracorporeal blood treatment can form a separate module which is operated alongside the extracorporeal blood treatment apparatus. The device according to the invention for the optimization comprises an input unit for inputting the patient- and machine-specific treatment parameters and a computing unit as well as a display unit for displaying the costs resulting for the extracorporeal blood treatment. It is however also possible for the device according to the invention to be a component of an extracorporeal blood treatment apparatus. If the device according to the invention is a component of an extracorporeal blood treatment apparatus, the device according to the invention can make use of the input unit, display unit and/or computing unit of the extracorporeal blood treatment apparatus.

In a preferred embodiment of the invention, the machine-specific treatment parameter, which is determined for the different types of dialyzer or filter, is the dialyzing fluid flow, which the doctor in charge sets for the performance of the blood treatment. In principle, however, machine-specific treatment parameters other than the extracorporeal blood flow can also be determined for all types of dialyzer or filter.

In order to determine the cost of the extracorporeal blood treatment for all types of dialyzer or filter, the method according to the invention and the device according to the invention preferably make provision to store in a memory unit the costs for the various types of dialyzer or filter and the costs for the consumables and/or the energy costs. The various costs can preferably be inputted on the input unit and then read into the memory unit, so that the costs can be changed at any time. Both the costs of the consumables and the energy costs are preferably taken into account in the ascertainment of costs. It is however also possible to take account solely of the costs of the consumables or the energy costs.

The method according to the invention and the device according to the invention preferably make provision to calculate with a computing unit the quantity of the respective consumables and/or the quantity of energy that is consumed in the performance of the extracorporeal blood treatment with the ascertained machine-specific treatment parameter. From the costs of the consumables and/or energy costs on the one hand and the calculated quantity of consumables and/or energy on the other hand, a calculation is made in the computing unit of the costs of the consumables and/or energy consumed in the extracorporeal blood treatment. The computing unit also calculates, for all types of dialyzer or filter, the total cost in each case from the sum of the stored cost of the respective dialyzer or filter and the calculated costs of the consumables and/or energy consumed in the blood treatment.

A further preferred embodiment makes provision such that the display unit displays the different amounts of the machine-specific treatment parameter for the different dialyzers or filters together with the total cost of the extracorporeal blood treatment resulting from the use of the given dialyzer or filter and the adjustment of the given machine-specific treatment parameter, so that the doctor in charge can make a choice between the various dialyzers or filters, taking account of the overall cost of the treatment. The overall cost is preferably broken down on the display unit into the costs resulting from the dialyzer or filter, the consumables and the consumed energy.

BRIEF DESCRIPTION OF THE DRAWINGS

An example of embodiment of the invention is explained in greater detail below by reference to the drawings.

In the figures.

DETAILED DESCRIPTION OF THE DRAWINGS

Figure 1:
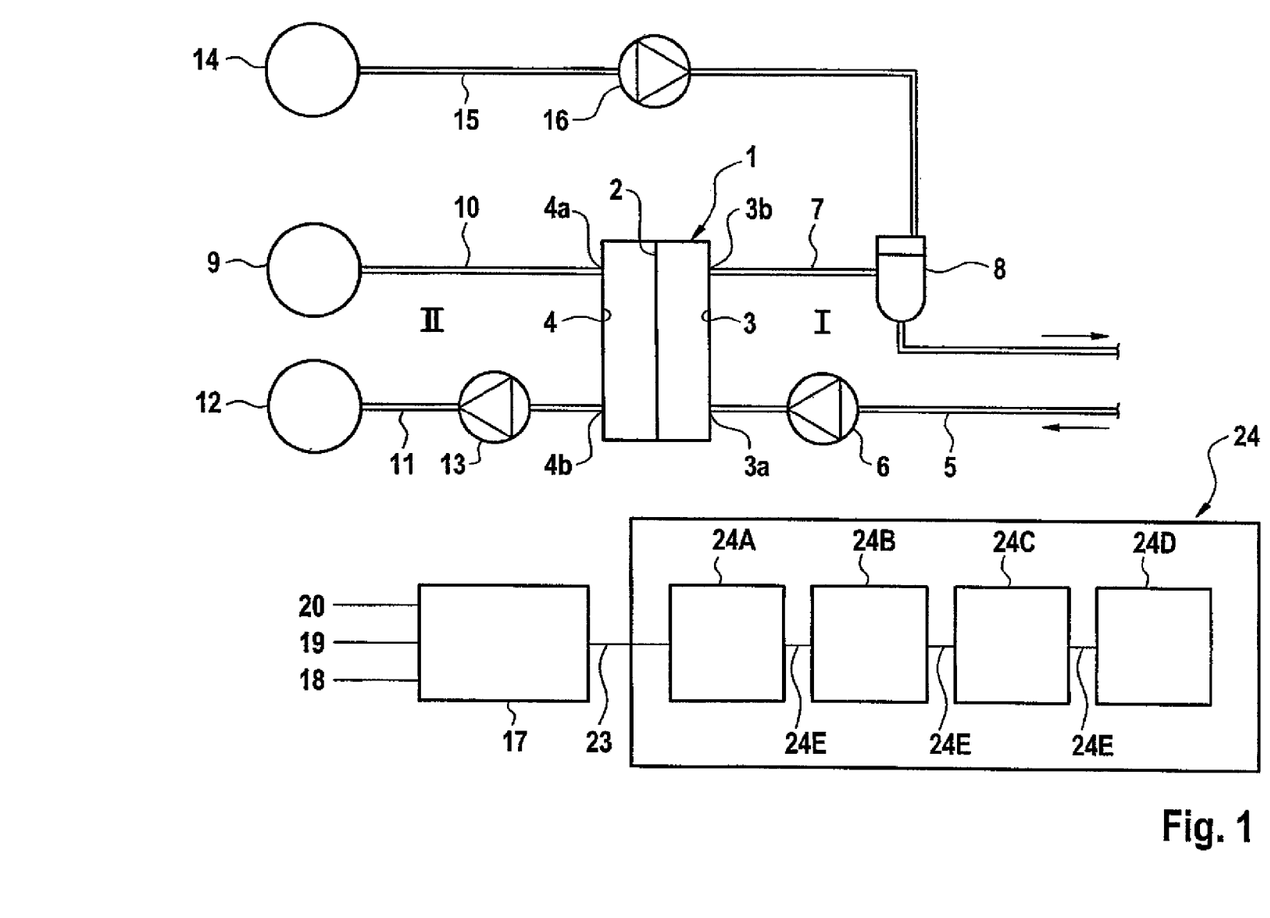
FIG. 1 shows the main components of an extracorporeal blood treatment apparatus together with a device for optimizing the blood treatment in a very simplified schematic representation.

FIG. 1 shows in a very simplified schematic representation the components of an extracorporeal blood treatment apparatus which are relevant to the invention and which can be operated both as a hemodialysis apparatus and/or a hemofiltration apparatus. The extracorporeal blood treatment apparatus will therefore be referred to in the following as a hemodiafiltration apparatus. The hemodiafiltration apparatus comprises a dialyzer or filter 1, which is separated by a semipermeable membrane 2 into a blood chamber 3 and a dialyzing fluid chamber 4. Inlet 3a of the blood chamber is connected to one end of an arterial blood supply line 5, into which a blood pump 6 is incorporated, whilst outlet 3b of the blood chamber is connected to one end of a venous blood return line 7, into which a drip chamber 8 is incorporated. Arterial and venous cannulas (not shown) for connection to the patient are present at the other ends of arterial and venous blood line 5, 7. This part of the fluid system represents extracorporeal blood circuit I of the hemodiafiltration apparatus.

Dialyzing fluid system II of the hemodiafiltration apparatus comprises a device 9 for the preparation of fresh dialyzing fluid, which is connected via a dialyzing fluid supply line 10 to inlet 4a of dialyzing fluid chamber 4 of dialyzer 1 or filter. Leading away from outlet 4b of dialyzing fluid chamber 4 of dialyzer 1 or filter is a dialyzing fluid return line 11, which leads to a drain 12. A dialyzing fluid pump 13, which is disposed in dialyzing fluid return line 11, is used to convey the dialyzing fluid.

Furthermore, the hemodiafiltration apparatus comprises a substituate source 14, from which a substituate line 15, into which a substituate pump 16 is incorporated, leads to venous drip chamber 8. A predetermined quantity of substitution fluid can be fed from substituate source 14 to extracorporeal blood circuit I by means of substituate pump 16 when fluid is removed from the blood circuit via dialyzer 1.

The hemodiafiltration apparatus further comprises a control and computing unit 17, which is connected via control lines 18, 19, 20 to blood pump 6, dialyzing fluid pump 13 and substituate pump 16. Central control and computing unit 17 controls pumps 6, 13 and 16 in such a way that a specific blood flow rate $Q_b$ is adjusted in extracorporeal blood circuit I and a specific dialyzing fluid rate $Q_d$ is adjusted in the dialyzing fluid system II. The control and computing unit also preselects a specific substituate rate and adjusts the ultrafiltration rate with which fluid is removed from the patient. The individual treatment parameter with which the extracorporeal blood treatment is to be carried out can be inputted by the doctor in charge on an input unit (not shown).

The device according to the invention for optimizing the blood treatment, which can form an independent unit or be a component of the extracorporeal blood treatment apparatus, will be described below. When the device for optimizing the blood treatment is a component of the blood treatment apparatus, the device for optimizing the blood treatment can make use of the components which are already present in the blood treatment apparatus. For example, the device for optimizing the blood treatment can make use of central computing and memory unit 17.

In the present example of embodiment, device 24 for optimizing the blood treatment comprises its own computing unit 24A, its own memory unit 24B and a separate input unit 24C and separate display unit 24D, which are connected to one another via data lines 24E. Device 24 is connected via a further data line 23 to central computing and control unit 17. Computing and memory unit 24A, 24B can form part of a central data processing system on which a data processing program runs, wherein input unit 24C can be a keyboard and display unit 24D a display screen.

Figure 2:
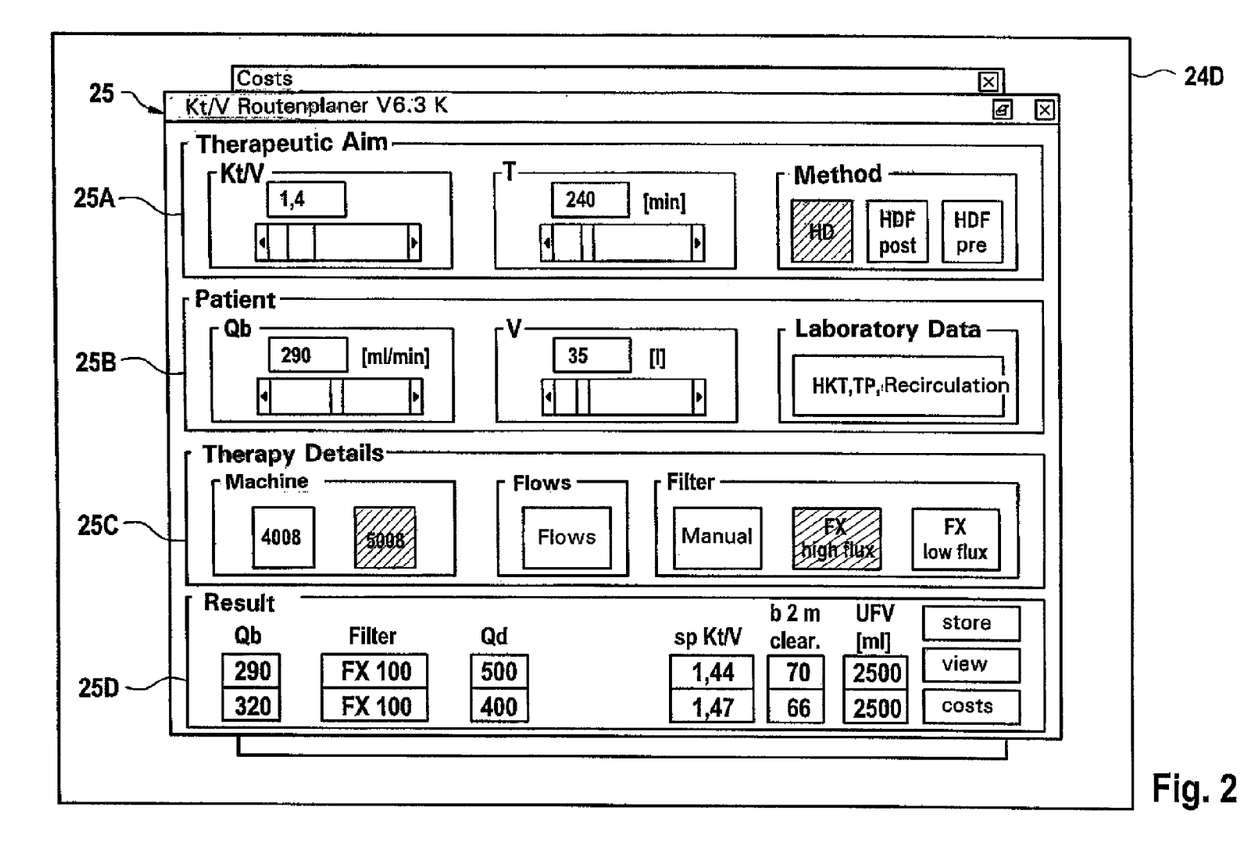
FIG. 2 shows the display unit of the device for optimizing the blood treatment, wherein the display unit displays the dialyzer or filter with which the total cost of the treatment is minimal.

FIG. 2 shows display screen 24D of the device according to the invention. The display screen displays the treatment parameters which are inputted by the doctor in charge on input unit 24C or which are calculated by computing unit 24A. The parameters are displayed on the display screen with the aid of masks 25.

In the present example of embodiment, the doctor in charge first preselects the patient-specific treatment parameters which are characteristic of the therapeutic aim and the patient to be treated. The treatment parameters characteristic of the therapeutic aim are displayed on the display screen in input mask 25 in first line 25A, whilst the parameters characteristic of the patient are displayed in line 25B. The therapeutic aim is preselected by the doctor with the treatment parameters of dialysis dose Kt/V, treatment duration T and the treatment method: hemodialysis HD, hemodiafiltration HDF with post-dilution $HDF_{post}$ or pre-dilution $HDF_{pre}$. The doctor preselects for the patient a specific blood flow $Q_b$, a specific urea distribution volume V and various other laboratory data, which can include for example hematocrit HKT. A tolerated deviation from the target value can be preselected for dialysis dose Kt/V.

In the present example of embodiment, 1.4 is preselected for dialysis dose Kt/V, 240 min for treatment time T, hemodialysis HD for the treatment method, 290 ml/min for blood flow $Q_b$ and 35l for urea distribution volume V. Furthermore, 2% is preselected as the tolerated deviation from the target value for dialysis dose Kt/V.

Furthermore, the doctor can preselect whether high-flux dialyzers or filters or low-flux dialyzers or filters should preferably be used. The doctor can also preselect the type of blood treatment apparatus. This is set in column 25C of mask 25. Here, the doctor has preselected high-flux dialyzers or filters and selected a dialysis machine of type 5008, which can be displayed by color background of the individual fields. In order to prompt the doctor to consider an increase in the blood flow, a further value for the blood flow can be inputted which is greater than the first value. The subsequent calculation then takes place for the lower and the higher blood flow. Here, the doctor has inputted 320 ml/min for increased blood flow $Q_b$. Both blood flows are displayed in column 25D.

Since an increase in the dialyzing fluid flow above a preselected upper threshold value does not lead in practice to a significant increase in clearance K, an upper threshold value can be preselected for the dialyzing fluid flow. In the case of patients with a small distribution volume V, it may happen that the target value for dialysis dose Kt/V is already reached with a dialyzing fluid flow that is smaller than the blood flow. In such cases, a dialyzing fluid flow can be preselected that is equal to the blood flow. A preselected lower threshold value can also be preselected for the dialyzing fluid flow. The pre-selection of upper and lower threshold values for the dialyzing fluid flow or blood flow is however only an option.

Device 24 according to the invention for optimizing the blood treatment now determines, both for the preselected lower blood flow and the higher blood flow of 290 and 320 ml/min respectively, the type of dialyzer or filter with which the cost of the dialysis treatment is minimal with a specific dialyzing fluid flow $Q_d$. In the present example of embodiment, the device suggests, for optimization of the blood treatment, a filter of type FX 100 with a dialyzing fluid flow $Q_d$ of 500 ml/min when blood flow $Q_b$ is 290 ml/min. When blood flow $Q_b$ is 320 ml/min, the device also suggests a filter of type FX 100, dialyzing fluid flow $Q_d$ however being 400 ml/min. The way in which the data are evaluated is described in detail below.

In memory unit 24B, a specific blood flow range $Q_{b1}$ to $Q_{b2}$ is assigned in each case to different dialyzers or filters from a group of dialyzers or filters. The group of dialyzers or filters comprises two kinds of filters, which include the high-flux filters and the low-flux filters. The high-flux filters for example include the type series FX 50, FX 60, FX 80 and FX 100.

On the basis of the type of dialyzer or filter selected by the doctor, for example a high-flux filter, and desired blood flow $Q_b$, those filters are selected from the respective type series that are in principle suitable for desired blood flow $Q_b$.

Example 1: Selected FX high-flux, $Q_b$=220 ml/min: FX 50 to FX 100 are possible.

Example 2: Selected FX high-flux, $Q_b$=370 ml/min: FX 60 to FX 100 are possible.

From the preselected value for dialysis dose KT/V, for example 1.40, inputted treatment time T and inputted urea distribution volume V, computing unit 24A next calculates a target value for clearance K. When the target value for clearance K is calculated, the preselected tolerance, for example 2%, is taken into account in the preselected target value for dialysis dose KT/V, so that a value for dialysis dose KT/V within the preselected tolerance can be accepted in the subsequent calculation of the cost of the treatment. In individual cases, cost savings can thus be made without this having demonstrable effects on the success of the treatment in practice.

When the target value for clearance K is determined, computing unit 24A calculates, for all the dialyzers or filters that have been determined beforehand, dialyzing fluid flow $Q_d$ required in each case for the treatment, taking account of the preselected treatment method, for example HD, $HDF_{post}$, $HDF_{pre}$, preselected blood flow $Q_b$ and other parameters, which include for example hematocrit HKT. From previously determined clearance K and preselected blood flow $Q_b$, the computing unit calculates dialyzing fluid flow $Q_d$ that is required to achieve desired clearance K. The calculation of required dialyzing fluid flow $Q_d$ is carried out for an HD treatment with coefficient k0A on the basis of the following equation:

$$K = Q_b Q_d \frac{1 - \exp\left(-k0A \frac{Q_d - Q_b}{Q_d Q_b}\right)}{Q_d - Q_b \exp\left(-k0A \frac{Q_d - Q_b}{Q_d Q_b}\right)}$$

For other types of treatment, such as for example HDF, other equations can be used to calculate K. Coefficient k0A is a magnitude characteristic of the given dialyzer or filter, which is essentially dependent on the active surface of the semipermeable membrane of the dialyzer or filter and its diffusion resistance.

Stored in memory unit 24B for all dialyzers or filters are the respective coefficients k0A, which are read out from the memory by computing unit 24A in order to calculate dialyzing fluid rate $Q_d$. The aforementioned method for determining the dialyzing fluid rate is described in detail in WO 2007/140993 A1, to the disclosure whereof reference is expressly made. For the invention, however, the method by which the dialyzing fluid rate is determined is ultimately irrelevant.

Furthermore, the costs of various consumables and the energy costs are stored in memory unit 24B. All the necessary costs (selling prices) can be inputted using appropriate menus. In the present example of embodiment, the costs of the consumables include the costs for permeate, acid and bicarbonate and the energy costs include the costs for electricity. The costs (selling prices) of the individual dialyzers or filters are also stored in memory unit 24B.

For all the dialyzers or filters which are suggested for the blood treatment, computing unit 24B calculates the quantity of the given consumables (permeate, acid, bicarbonate) and the quantity of energy (electricity) that is consumed in the blood treatment, taking account of given dialyzing fluid rates $Q_d$ and preselected blood flow rates $Q_b$.

From the calculated quantity of consumables and the stored costs of consumables as well as the consumed energy and the energy costs, computing unit 24A now calculates the costs for all the consumables and the costs for the energy consumed in the treatment. Finally, the computing unit calculates the total costs for all types of dialyzers or filters in each case from the sum of the previously determined costs for the consumables consumed in the treatment and the costs for the consumed energy as well as the costs of the dialyzers or filters.

The final selection of the dialyzer or filter is then made on the premise that the total cost is minimal.

Figure 3:
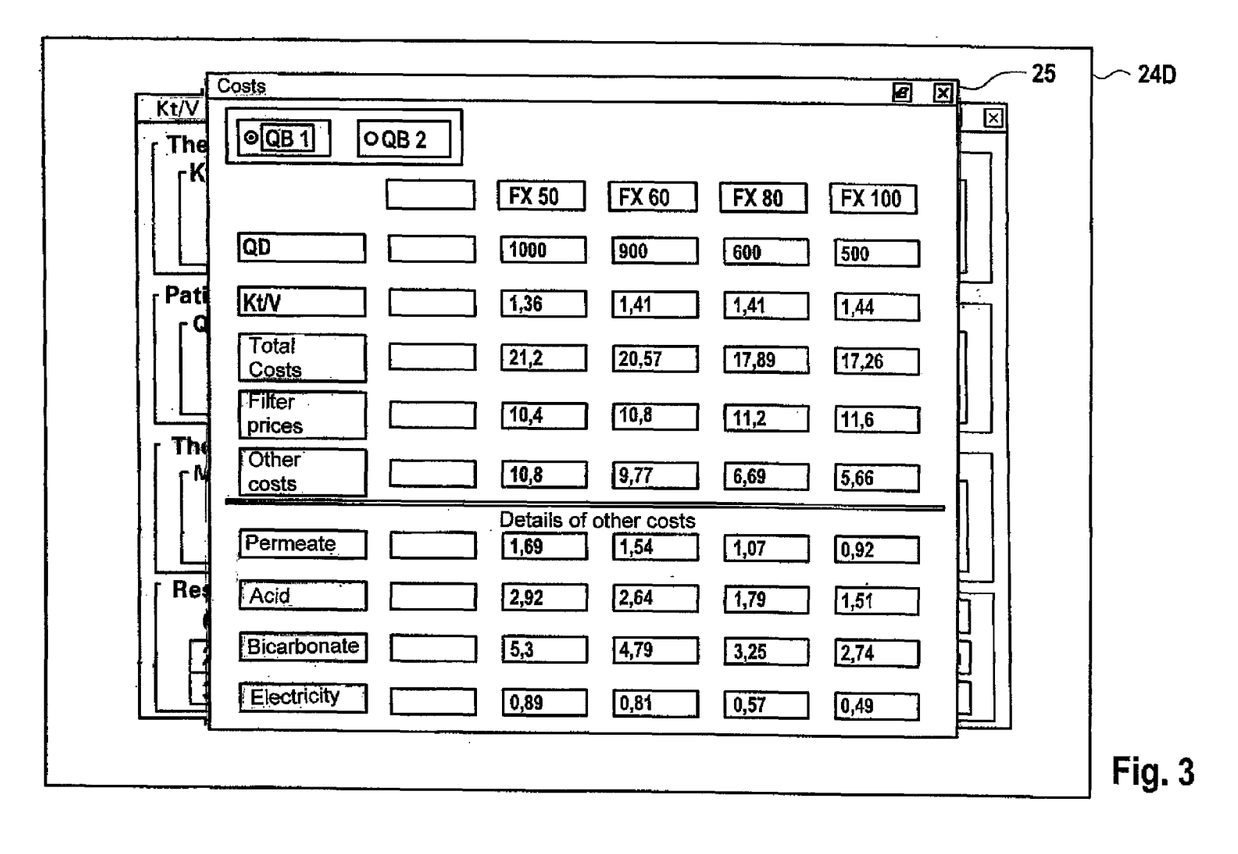
FIG. 3 shows the display unit of the device for optimizing the blood treatment, wherein the costs are displayed for the blood treatment with a first blood flow rate for different types of dialyzer or filter.

Via the menu item "costs", the doctor can call up a sub-menu in which the individual costs for the suggested dialyzers or filters are shown. FIG. 3 shows the sub-menu for the present example of embodiment, in which blood flow $Q_b$ of 290 ml/min ($Q_b$ 1) is preselected (FIG. 2).

In the cost presentation, all the dialyzers or filters which are suitable for the intended blood flow are always displayed in columns. In the present example of embodiment, in which a blood flow of 290 ml/min is preselected, these are the high-flux dialyzers FX 50 to FX 100. A color background of the menu items is used to identify those dialyzers or filters with which the target value for dialysis dose Kt/V cannot be achieved, with which the target value for the dialysis dose can only be achieved with a relatively high dialyzing fluid flow or with a relatively low dialyzing fluid flow. In the present example of embodiment, filter FX 50 is identified with the color red, since the target value for the dialysis dose of 1.40 cannot be achieved with this filter. Filter FX 60 is identified with the color yellow, since the target value for the dialysis dose can only be achieved with this filter with a relatively high dialyzing fluid flow amounting to more than 1.5 times the blood flow. Filters FX 80 and FX 100, on the other hand, are identified with the color green, since the target value for the dialysis dose can be achieved with a relatively low dialyzing fluid flow with these filters. It can be seen in the present example of embodiment that the sum of the costs, which consist of the filter prices and the other costs, which include costs for permeate, acid, bicarbonate and electricity, is minimal with filter FX 100. Following a comparison of the various total costs, computing unit 24A therefore selects dialyzer FX 100 with which the total cost is minimal. The result is displayed in the main menu (FIG. 2: $Q_b$ 290, filter FX 100 $Q_d$ 500).

Figure 4:
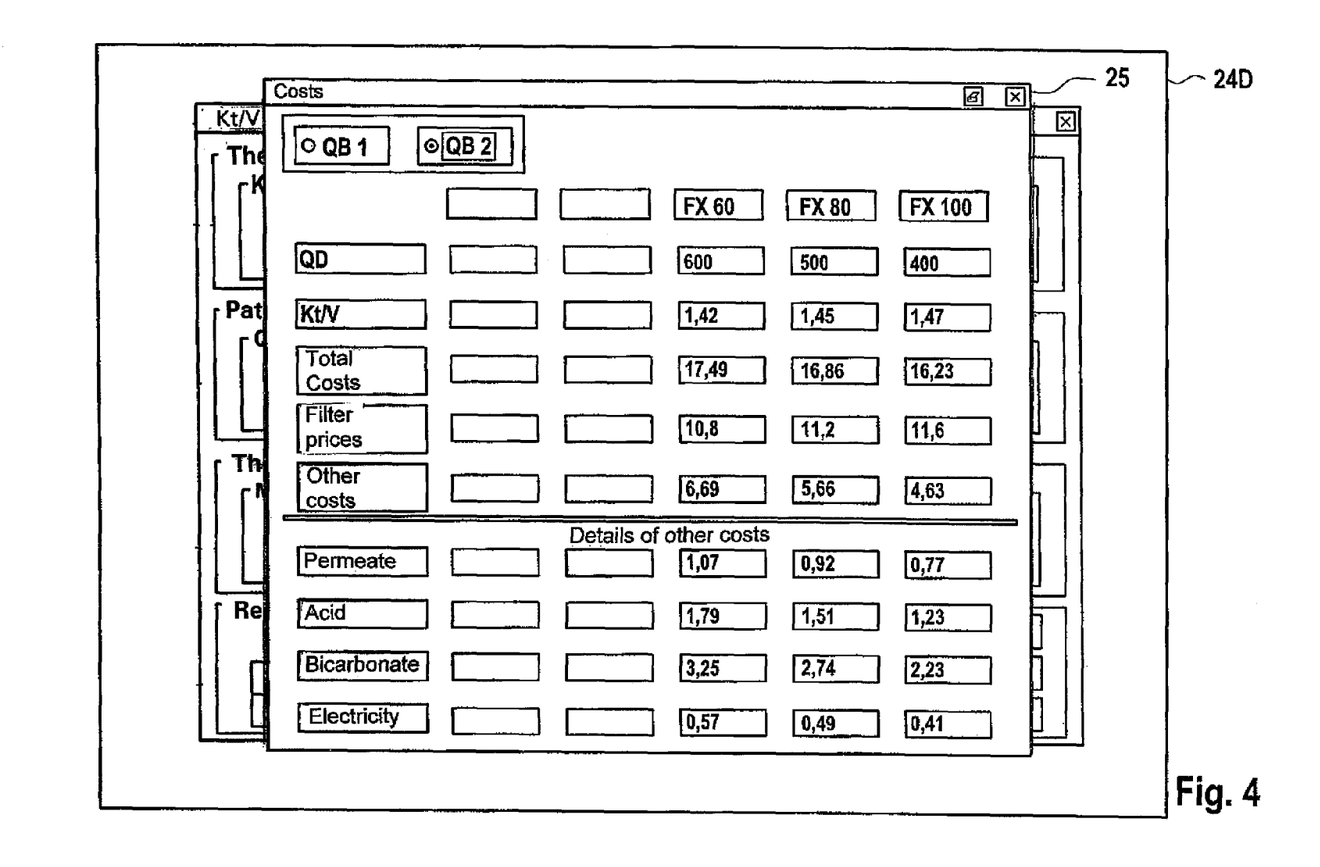
FIG. 4 shows the display unit, on which the costs of the blood treatment are displayed for a blood treatment with a second blood flow rate which is greater than the first blood flow rate, for the various types of dialyzer or filter.

FIG. 4 shows the sub-menu for the alternative higher blood flow of 320 ml/min ($Q_b$ 2). With the raised blood flow, it can be seen that filter FX 50 no longer comes into consideration. This filter is therefore no longer displayed in the mask. With the raised blood flow, the target value for dialysis dose Kt/V can already be achieved with a dialyzing fluid flow of 400 ml/min when filter FX 100 is used. The total cost of the treatment is also lowest with this filter. Consequently, the computing unit again suggests filter FX 100 also for the treatment with the higher blood flow of 320 ml/min (FIG. 2: $Q_b$ 320, filter FX 100 $Q_d$ 400). It is now left to the doctor's discretion whether he performs the treatment with filter FX 100 with the lower or higher blood flow at the higher or lower dialyzing fluid flow. The example of embodiment thus shows that the device according to the invention makes it particularly clear to the doctor what the effects will be of changing the blood flow or the treatment time.

Figure 5:
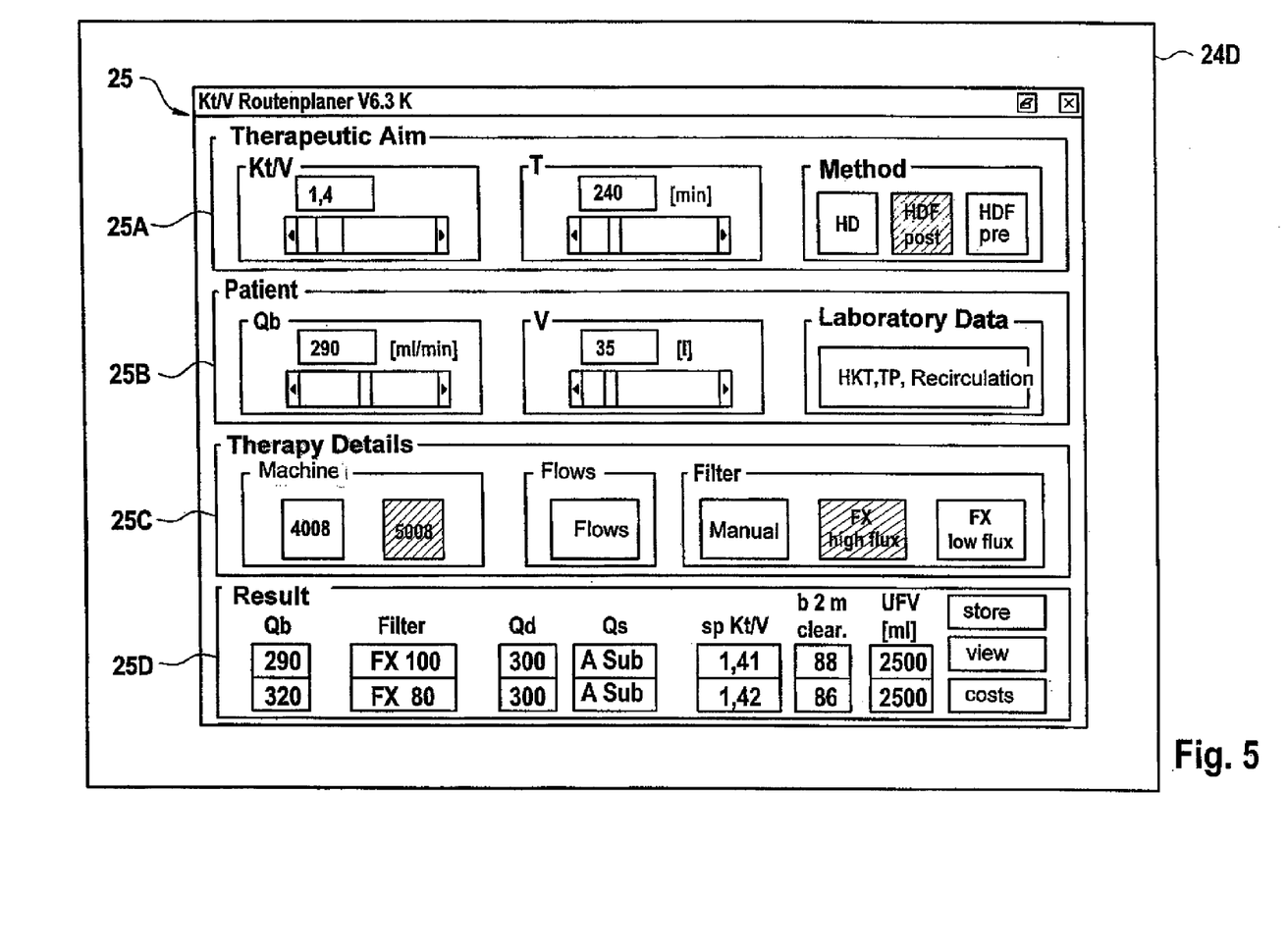
FIG. 5 shows the display unit with the pre-selection of different treatment parameters, the display unit displaying the dialyzer or filter with which the cost of the blood treatment is minimal.
Figure 6:
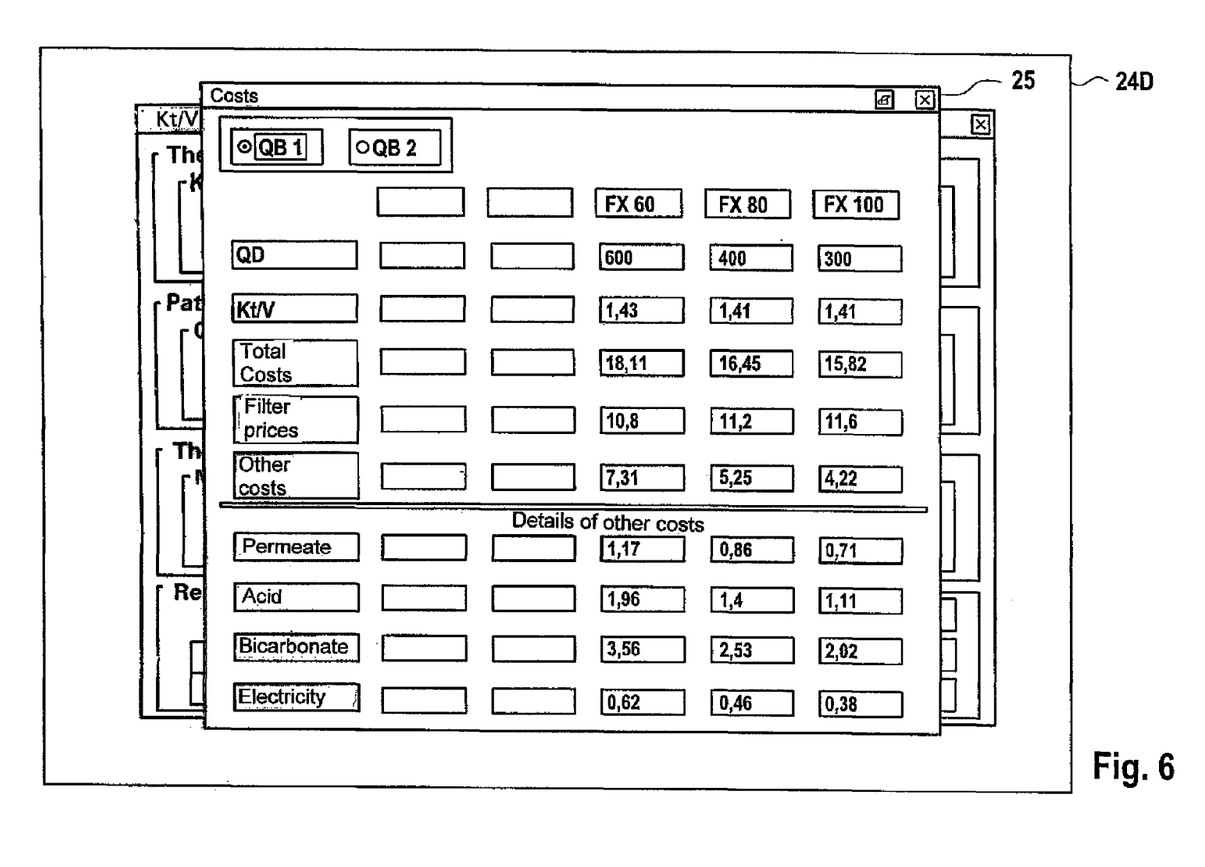
FIG. 6 shows the display unit of FIG. 5, the costs being displayed for the blood treatment with a first blood flow rate for various types of dialyzer or filter.
Figure 7:
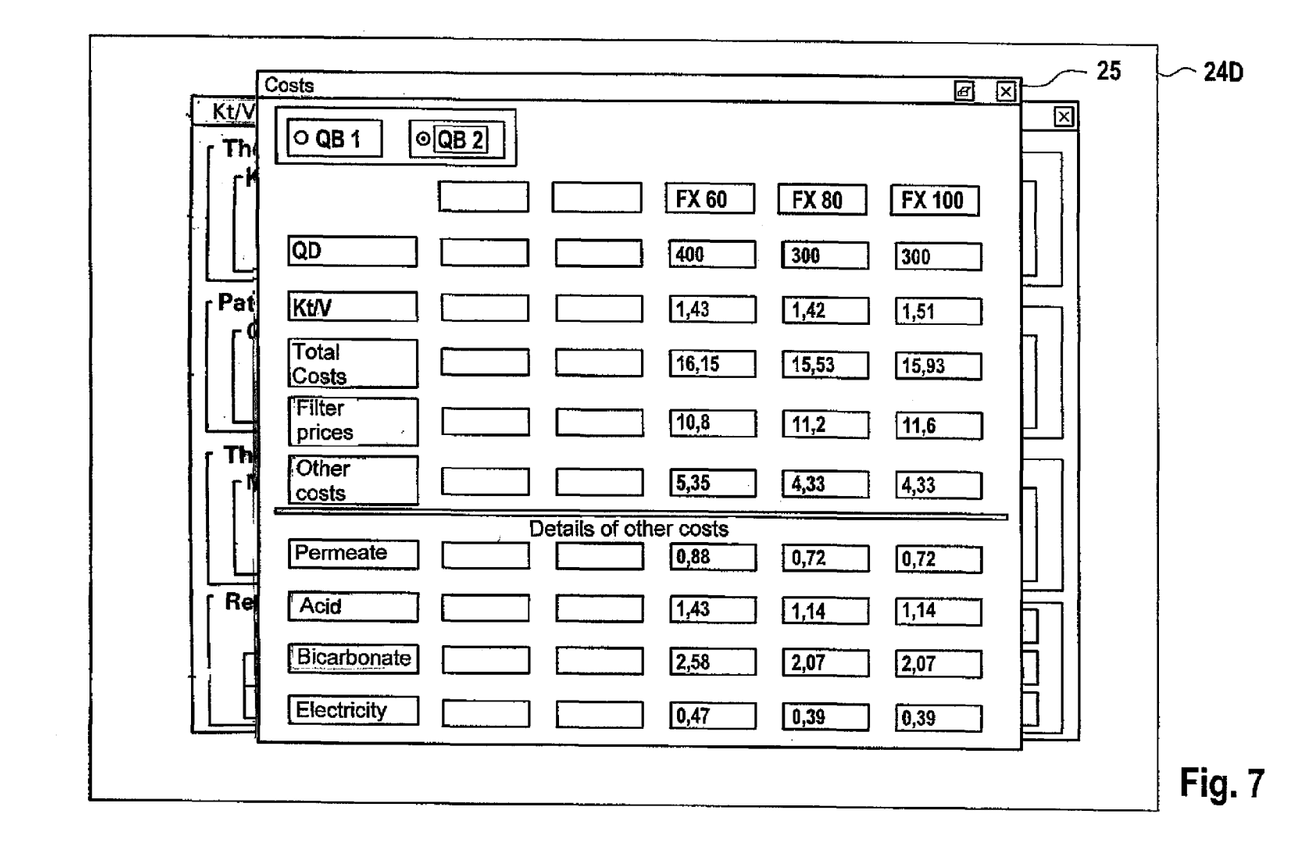
FIG. 7 shows the display unit of FIG. 5, on which the costs of the blood treatment are displayed for a blood treatment with a second blood flow rate which is greater than the first blood flow rate, for the various types of dialyzer or filter.

FIGS. 5 to 7 show the main menu and the two sub-menus, which are displayed on display unit 24D of the device according to the invention for optimizing the blood treatment, when it is not an HD treatment, but an HDF treatment (hemodiafiltration) with post-dilution ($HDF_{post}$) that is preselected. The treatment parameters are otherwise identical to the parameters with which the treatment is carried out in the first example of embodiment.

In the main menu (FIG. 5), filter FX 100 with a dialyzing fluid flow of 300 ml/min is suggested for blood flow $Q_b$ 290 ml/min and filter FX 80 for a blood flow $Q_b$ of 320 ml/min also with a dialyzing fluid flow of 300 ml/min, in order to keep the cost of the treatment as low as possible without abandoning the target value for the dialysis dose.

The sub-menu for blood flow $Q_b$ of 290 ml/min (FIG. 6) shows that a treatment is in principle possible with filters FX 60 to FX 100. For these filters, the computing unit calculates a dialyzing fluid flow which lies between 600 and 300 ml/min. The target value of the dialysis dose of 1.40 can be achieved with all the filters. The total cost of the treatment, however, is lowest with filter FX 100. The dialyzing fluid flow is also lowest with filter FX 100. The effect of an increase in the blood flow to 320 ml/min is that the total cost of the treatment is lowest with filter FX 80 (FIG. 7). The dialyzing fluid flow is also lowest with filter FX 80. This corresponds to the dialyzing fluid flow with filter FX 100 with the lowest blood flow. Making reference to FIGS. 8 to 11, the case is described where the therapeutic aim cannot be achieved even within the preselected tolerance for dialysis dose KT/V.

Figure 8:
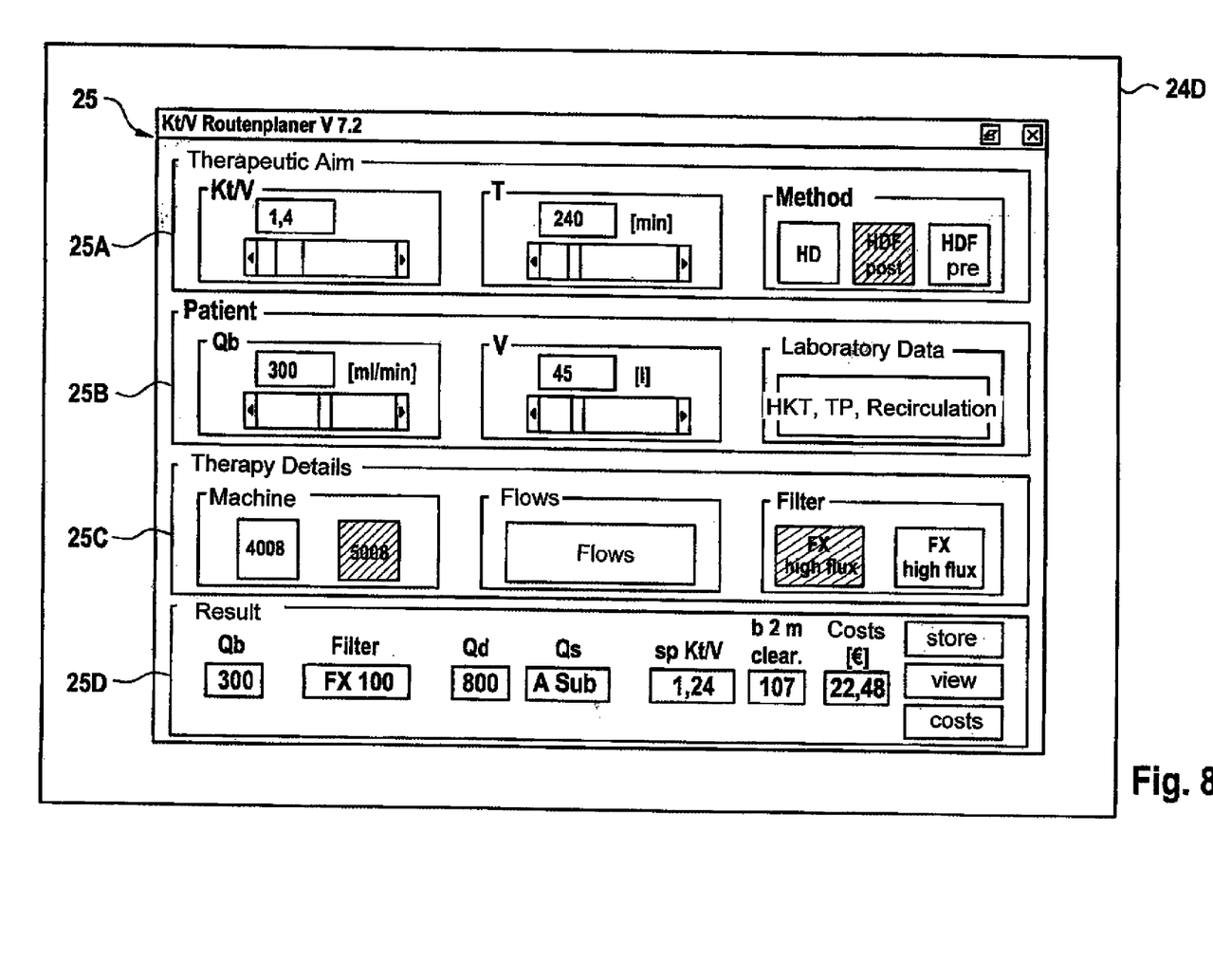
FIG. 8 shows the display unit, wherein the therapeutic aim is not achieved.

FIG. 8 shows display screen 24D, on which the preselected value for dialysis dose KT/V is displayed. The doctor has preselected a dialysis dose KT/V of 1.4. If the therapeutic aim is not achieved for example with low blood flow $Q_b$ or large distribution volume V, the doctor receives an indication. In the present example of embodiment, the achievable value for dialysis dose KT/V of 1.24, which lies below the preselected value of 1.4, i.e. also lies outside the preselected tolerance of 2%, is displayed on a red background. This thus signals that the therapeutic aim is not achieved.

In this case, the largest dialyzer and the highest dialyzing fluid flow $Q_d$ would always have to be selected in order to come as close as possible to the target value. Effective use of the means, however, is not therefore present.

Computing unit 24A in this case automatically performs a further optimization step, in which the value for dialysis dose KT/V, for example 1.24, reached in the first optimization step is preselected as the new target value. Computing unit 24A again takes a preselected tolerance, for example 2%, into account for the new target value.

Figure 9:
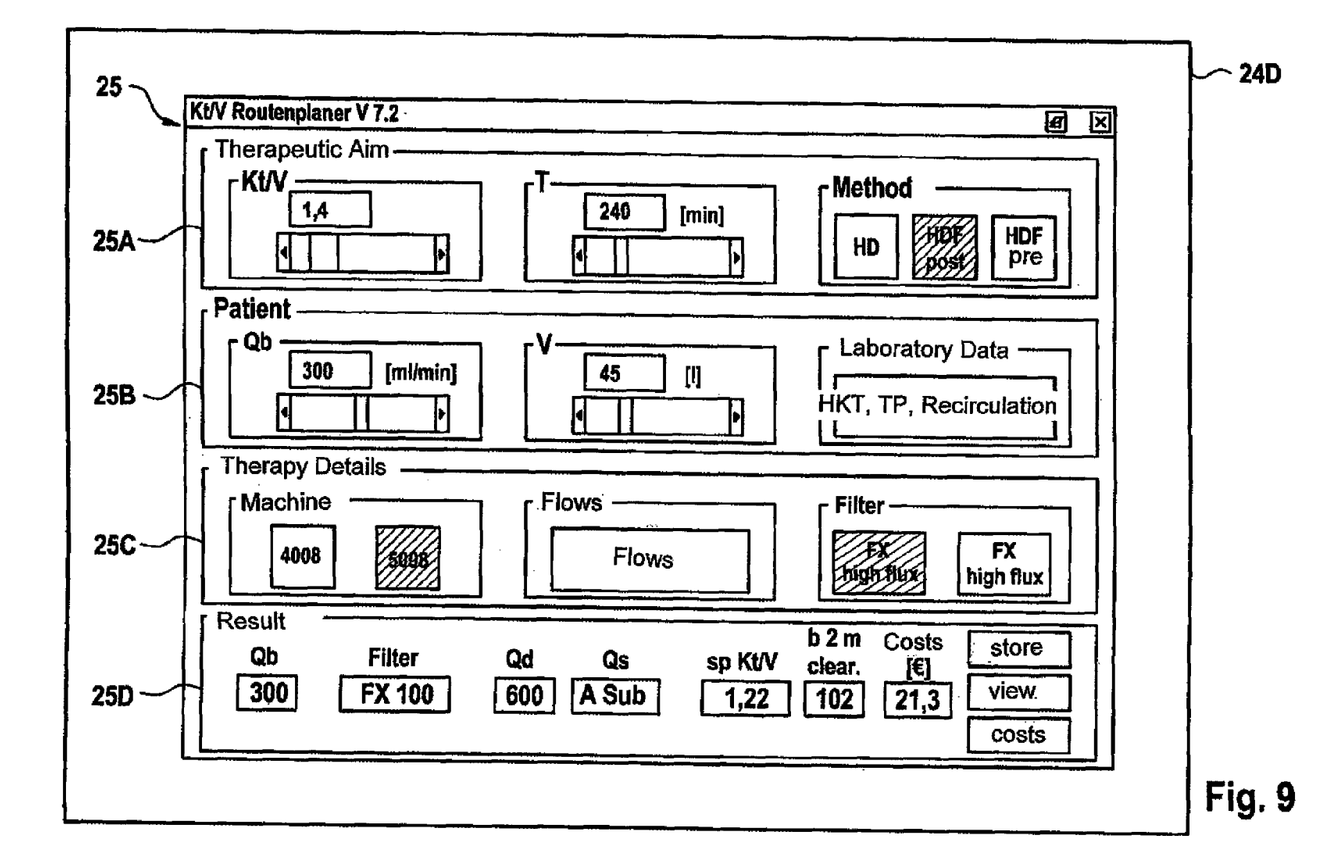
FIG. 9 shows the display unit after an optimization step for which the unachieved therapeutic aim is stipulated as the target value.

FIG. 9 shows display screen 24D, on which the result of the calculation in the second optimization step is displayed with a target value for dialysis dose KT/V of 1.24. It can be seen that a dialysis dose KT/V of 1.22 results, which again lies outside the preselected tolerance, but is only slightly less than the preselected target value of 1.24. Since the newly calculated value for dialysis dose KT/V again lies outside the tolerance, the value is again displayed on a red background. Computing unit 24A calculates the cost that is incurred with the preselected parameters that are displayed on display screen 24D. In the present example of embodiment, the cost amounts to EUR 21.30.

Figure 10:
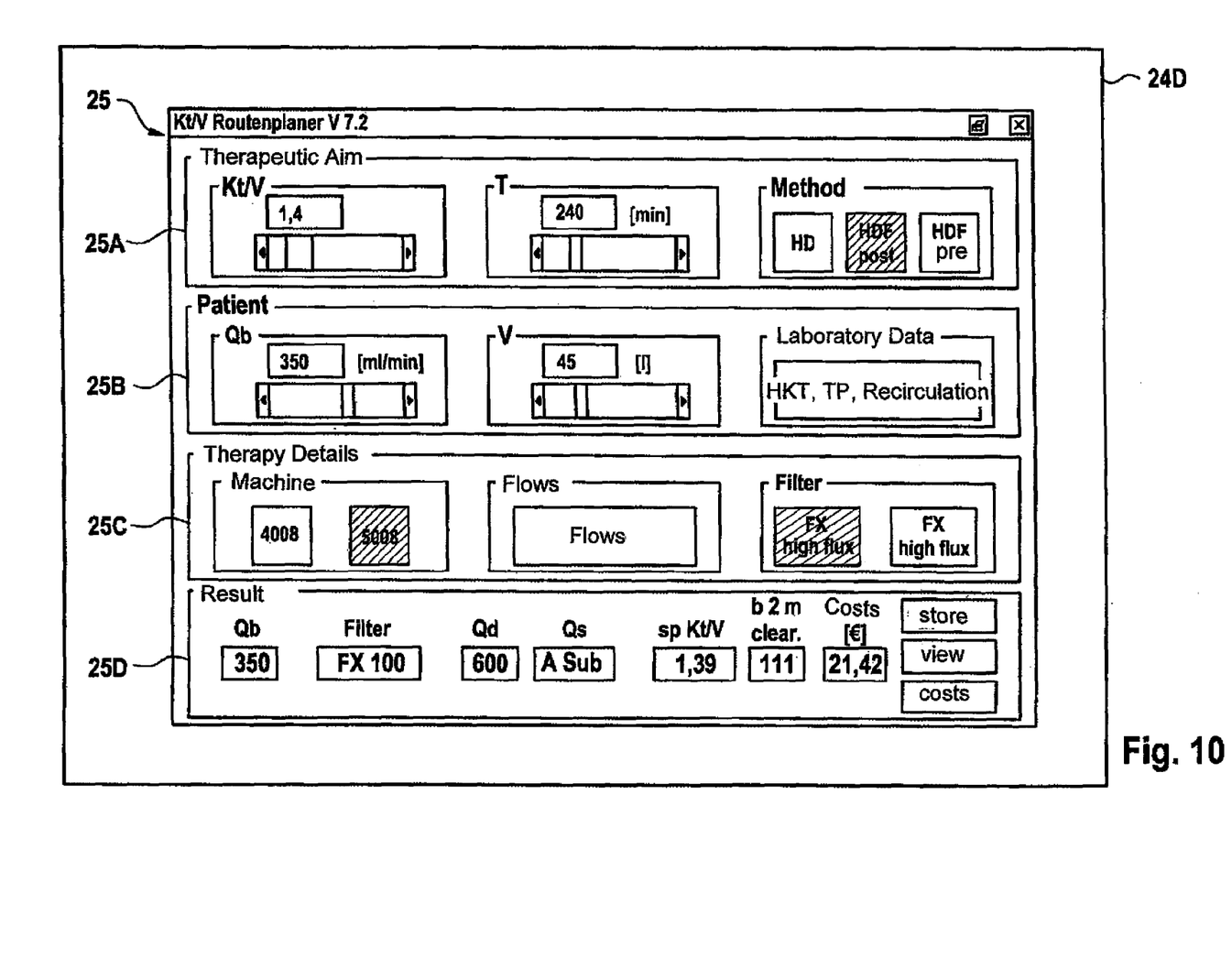
FIG. 10 shows the display unit, wherein the therapeutic aim is achieved with an increase in the blood flow rate.
Figure 11:
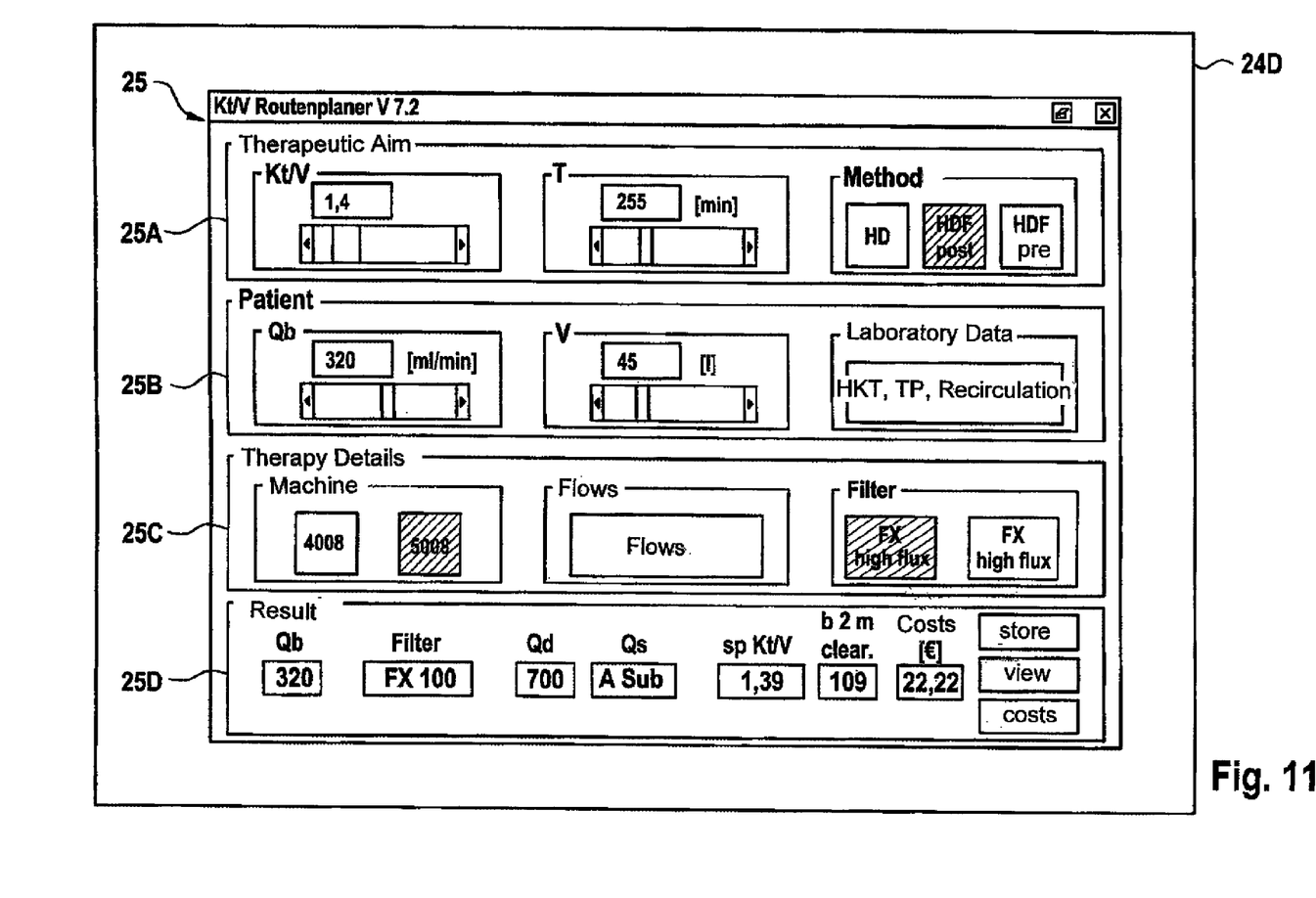
FIG. 11 shows the display unit, wherein the therapeutic aim is achieved with an increase in the blood flow rate and the treatment time.

FIGS. 10 and 11 show that an increase in dialysis dose KT/V to 1.4 can be achieved with an increase in blood flow $Q_b$ and/or treatment time T. For example, a dialysis dose KT/V of 1.39, which lies within the tolerance, can be achieved by the fact that blood flow $Q_b$ is increased from 300 to 350 ml/min with an identical treatment time T of 240 min (FIG. 10). A dialysis dose KT/V of 1.39 can however also be achieved with a blood flow $Q_b$ of 320 ml/min with a treatment time T of 255 (FIG. 11.). Computing unit 24A calculates the cost for the various pre-selections which amounts to EUR 21.42 (FIG. 10) and EUR 22.22 (FIG. 11), so that the doctor can make a decision as to the parameters with which the treatment should be carried out.

What is claimed is:

1. A method of selecting a dialyzer or filter for an extracorporeal blood treatment with an extracorporeal blood treatment apparatus, the extracorporeal blood treatment apparatus being configured to receive the dialyzer or filter and comprising a cost determination device, said method comprising:

providing the extracorporeal blood treatment apparatus, wherein the cost determination device comprises:
an input unit configured to input one or more patient-specific treatment parameters, wherein said patient-specific parameters are characteristic of a therapeutic aim, a patient to be treated, or both;
a computing unit configured to determine a machine-specific treatment parameter from the one or more patient-specific treatment parameters for performing the treatment using each dialyzer or filter from a group of different types of dialyzers or filters having different dialyzing fluid flows and further determine a cost of the extracorporeal blood treatment resulting from the machine-specific treatment parameter using each dialyzer or filter; and
a display unit configured to display a cost resulting from the machine-specific treatment parameter using each dialyzer or filter from the group of different types of dialyzers or filters, the display unit comprising at least four display screen areas comprising:
a first screen area configured to display at least one therapeutic aim parameter,
a second screen area configured to display at least one patient parameter,
a third screen area configured to display at least one apparatus parameter, and
a fourth screen area configured to display a dialyzer or filter that would result in a lowest cost treatment;

inputting one or more patient-specific treatment parameters using the input unit, wherein said patient-specific treatment parameters are characteristic of the therapeutic aim, the patient to be treated, or both;
displaying the one or more inputted patient-specific treatment parameters in the second screen area;
displaying the group of different types of dialyzers or filters in the third screen area;
determining a respective machine-specific treatment parameter, from the one or more patient-specific treatment parameters, for performing the extracorporeal blood treatment, for each dialyzer or filter from the group of different types of dialyzers or filters displayed in the third screen area, using the computing unit;
calculating a quantity of the respective consumables or a quantity of energy that would be consumed in the performance of the extracorporeal blood treatment with the ascertained machine-specific treatment parameter, using the computing unit;
determining the cost of carrying out the extracorporeal blood treatment resulting from the ascertained machine-specific treatment parameter, based on the quantity of the respective consumables or the quantity of energy that would be consumed, for using each dialyzer or filter, using the computing unit;
displaying in the fourth screen area the respective cost that would result from carrying out the machine-specific treatment parameter using each dialyzer or filter displayed in the third screen area;
selecting the dialyzer or filter with the lowest cost resulting for carrying out the extracorporeal blood treatment; and
performing the extracorporeal blood treatment with the selected dialyzer or filter in the extracorporeal blood treatment apparatus.

2. The method according to claim 1, wherein the step of determining the cost of the extracorporeal blood treatment comprises the following steps:
storing the costs of each of the different types of dialyzers or filters in a memory unit, storing the costs of consumables or the energy costs in the memory unit; and
calculating the costs of the consumables or the cost of the energy consumed during the extracorporeal blood treatment, from the costs of the consumables or the energy costs, and from the calculated quantity of consumables or the calculated quantity of energy,
wherein the total cost for each dialyzer or filter is calculated with the computing unit from the sum of the stored costs of the respective dialyzer or filter and the calculated costs of the consumables or the energy consumed to carry out the extracorporeal blood treatment.

3. The method according to claim 1, further comprising displaying the different quantities of the machine-specific treatment parameter for the different dialyzers or filters, the total cost of the extracorporeal blood treatment resulting from the use of the given dialyzer or filter, and an adjustment of the given machine-specific treatment parameter, on the display unit.

4. The method according to claim 1, wherein the machine-specific treatment parameter comprises dialyzing fluid flow with which dialyzing fluid flows through the second chamber of the dialyzer or filter.

5. The method according to claim 1, wherein the one or more patient-specific treatment parameters are selected from the group consisting of: blood distribution volume V, duration T of the extracorporeal blood treatment, the dialysis dose, clearance K, and blood flow $Q_b$ in the extracorporeal blood circuit.

6. The method according to claim 1, further comprising:
highlighting in the fourth screen area the dialyzer or filter that would result in the lowest cost for carrying out the extracorporeal blood treatment.

7. The method according to claim 1, wherein the group of different types of dialyzers or filters includes at least one high-flux dialyzer or filter and at least one low-flux dialyzer or filter.

8. An extracorporeal blood treatment apparatus, comprising:
a control and computing unit;
a blood pump;
a dialyzing fluid pump;
control lines connecting the control and computing unit to the blood pump and the dialyzing fluid pump;
a connection for a dialyzer or filter that is divided by a semipermeable membrane into a first chamber and a second chamber, wherein the first chamber is part of an extracorporeal blood circuit and the second chamber is part of a dialyzing fluid system; and
a cost determination device comprising an input unit configured to input one or more patient-specific treatment parameters, wherein said one or more patient-specific treatment parameters are characteristic of a therapeutic aim, a patient to be treated, or both, wherein the control and computing unit is configured to determine a machine-specific treatment parameter from the one or more patient-specific treatment parameters for performing an extracorporeal blood treatment using each respective dialyzer or filter from a group of different types of dialyzers or filters having different dialyzing fluid flows, the control and computing unit being further configured to determine a cost of the extracorporeal blood treatment based on calculating a quantity of the respective consumables or a quantity of energy that would be consumed, resulting from the machine-specific treatment parameter, using each dialyzer or filter; and
a display unit configured to display the respective cost resulting from the machine-specific treatment parameter using each respective dialyzer or filter from the group of different types of dialyzers or filters, the display unit comprising at least four display screen areas comprising:
a first screen area configured to display at least one therapeutic aim parameter,
a second screen area configured to display at least one patient parameter,
a third screen area configured to display at least one apparatus parameter, and
a fourth screen area configured to display a dialyzer or filter that would result in a lowest cost treatment,
wherein the control and computing unit is configured to select the dialyzer or filter that would result in the lowest cost for carrying out the extracorporeal blood treatment; and
the selected dialyzer or filter is configured to perform the extracorporeal blood treatment.

9. The treatment apparatus according to claim 8, wherein the group of different types of dialyzers or filters includes at least one high-flux dialyzer or filter and at least one low-flux dialyzer or filter.

10. The extracorporeal blood treatment apparatus of claim 8, further comprising an extracorporeal blood treatment apparatus input unit configured to input an individual treatment parameter with which the extracorporeal blood treatment is to be carried out, wherein the extracorporeal blood treatment apparatus input unit comprises the input unit configured to input the one or more patient-specific treatment parameters to the cost determination device.

11. The extracorporeal blood treatment apparatus of claim 8, further comprising an extracorporeal blood treatment apparatus display unit, wherein the extracorporeal blood treatment apparatus display unit comprises the display unit of the cost determination device.

12. The extracorporeal blood treatment apparatus of claim 8, wherein the input unit comprises a keyboard.

13. The extracorporeal blood treatment apparatus of claim 8, wherein the display unit comprises a display screen and the display screen comprises the at least four display screen areas.

* * * * *